United States Patent
Kon et al.

(10) Patent No.: US 10,500,567 B2
(45) Date of Patent: Dec. 10, 2019

(54) USE OF RHENIUM-CONTAINING SUPPORTED HETEROGENOUS CATALYSTS FOR THE DIRECT DEOXY-DEHYDRATED OF GLYCEROL TO ALLYL ALCOHOL

(71) Applicants: CENTRE NATIONAL DE LA RECHERCHE SCIENTIFIQUE, Paris (FR); ECOLE CENTRALE DE LILLE, Villeneuve d'Ascq (FR); NATIONAL INSTITUTE OF ADVANCED INDUSTRIAL SCIENCE AND TECHNOLOGY, Tokyo (JP); UNIVERSITE DES SCIENCES ET TECHNOLOGIES DE LILLE-LILLE 1, Villeneuve d'Ascq (FR)

(72) Inventors: Yoshihiro Kon, Ibaraki (JP); Benjamin Katryniok, Meurchin (FR); Franck Dumeignil, Villeneuve d'Ascq (FR); Marcia Araque Marin, Lille (FR); Sébastien Paul, Thun Saint Amand (FR)

(73) Assignees: CENTRE NATIONAL DE LA RECHERCHE SCIENTIFIQUE, Paris, Villeneuve d'Ascq (FR); ECOLE CENTRALE DE LILLE, Villeneuve d'Ascq (FR); NATIONAL INSTITUTE, Tokyo (JP)

( * ) Notice: Subject to any disclaimer, the term of this patent is extended or adjusted under 35 U.S.C. 154(b) by 88 days.

(21) Appl. No.: 15/747,277

(22) PCT Filed: Jul. 27, 2016

(86) PCT No.: PCT/EP2016/067858
§ 371 (c)(1),
(2) Date: Jan. 24, 2018

(87) PCT Pub. No.: WO2017/017122
PCT Pub. Date: Feb. 2, 2017

(65) Prior Publication Data
US 2018/0207618 A1 Jul. 26, 2018

(30) Foreign Application Priority Data

Jul. 30, 2015 (EP) ..................... 15306244

(51) Int. Cl.
| | | |
|---|---|---|
| *C07C 29/60* | (2006.01) |
| *C07C 33/03* | (2006.01) |
| *B01J 23/36* | (2006.01) |
| *B01J 21/04* | (2006.01) |
| *B01J 35/10* | (2006.01) |
| *B01J 37/02* | (2006.01) |

(52) U.S. Cl.
CPC .............. *B01J 23/36* (2013.01); *B01J 21/04* (2013.01); *B01J 35/1019* (2013.01); *B01J 37/0201* (2013.01); *C07C 29/60* (2013.01)

(58) Field of Classification Search
CPC .. C07C 29/60; B01J 23/36; B01J 21/04; B01J 35/1019; B01J 37/0201
See application file for complete search history.

(56) References Cited

FOREIGN PATENT DOCUMENTS

DE    1002008031828 A  *  7/2008  .............  C07C 29/60

OTHER PUBLICATIONS

International search report dated Jan. 21, 2016.
Deoxydehydration of glycerol to allyl alcohol catalyzed by rhenium derivatives dated May 2014, Cat. Sci. Tech. ,vol. 4, pp. 3697-3704.

* cited by examiner

*Primary Examiner* — Rosalynd A Keys
(74) *Attorney, Agent, or Firm* — Ipsilon USA, LLP

(57) ABSTRACT

The present invention relates to the use of rhenium-containing supported heterogeneous catalysts for the deoxydehydration of glycerol to allyl alcohol, as well as to a process for the production of allyl alcohol from glycerol, in the presence of such heterogeneous catalysts.

11 Claims, No Drawings

USE OF RHENIUM-CONTAINING SUPPORTED HETEROGENOUS CATALYSTS FOR THE DIRECT DEOXY-DEHYDRATED OF GLYCEROL TO ALLYL ALCOHOL

RELATED APPLICATION

This application is a National Phase of PCT/EP2016/067858, filed on Jul. 27, 2016, which in turn claims the benefit of priority from European Patent application No. 15 306 244.3, filed on Jul. 30, 2015 the entirety of which are incorporated by reference.

FIELD OF THE INVENTION

The present invention relates to the use of rhenium-containing supported heterogeneous catalysts for the direct deoxydehydration of glycerol to allyl alcohol, as well as to a process for the production of allyl alcohol from glycerol, in the presence of such heterogeneous catalysts.

DESCRIPTION OF THE RELATED ART

Allyl alcohol is known as a valuable material in the chemical industry. It can be used as such, but also as a raw material to produce a variety of high tonnage chemicals such as acrolein, acrylic acid or acrylonitrile. It is also used as an allylating agent in modern organic chemistry (Sundararaju et al., Chem. Soc. Rev., 2012, 41, 4467-4483).

Currently, allyl alcohol is obtained by selective hydrogenation of acrolein itself most conventionally issued from a propylene selective oxidation process. Therefore, the allyl alcohol synthesis is today dependent from propylene, which is a product issued from fossil resources, in particular from petroleum refining, of which the supply is further threatened by an unbalanced offer/demand issue.

Alternative processes not involving the use of propylene have been investigated.

Glycerol is one of the most important renewable platform molecules because it is a co-product of the transesterification process for biodiesel production (about 100 kg of glycerol are produced per ton of biodiesel). The recent market expansion of biodiesel has resulted in a glut of glycerol, whereby it has become very attractive as a substrate for the synthesis of more valuable chemicals.

Hence, effective conversion processes from glycerol to useful chemicals are intensively being studied all over the world. These reactions generally require catalysts. For instance to get acrolein from glycerol, catalysts with appropriate acidity are necessary, and intensive research activities have been focused on the use of, e.g., zeolites, heteropolyacids, mixed metal oxides and (oxo)-pyrophosphates, as their acidic properties are well-known (Katryniok et al., Green Chem., 2010, 12, 2079).

Among the different molecules derived from glycerol, allyl alcohol is known as an important chemical intermediate for producing resins, paints, coatings, coupling agents, and so on. Allyl alcohol is also valuable as a starting material that can be catalytically converted to acrolein, acrylonitrile and acrylic acid among others. The processes of conversion of allyl alcohol to acrolein and/or acrylic acid are well established, but the efficient and sustainable generation of allyl alcohol from glycerol (and, generally speaking, from biosources) has never been performed in a practical manner.

Recently, different processes for the synthesis of allyl alcohol from glycerol using rhenium-based catalysts have been reported. For example, Canale V. et al. (Catal. Sci. Technol., 2014, 4, 3697-3704) report that the deoxydehydration (DODH) of glycerol to allyl alcohol is catalyzed by rhenium derivatives, either in neat glycerol or in the presence of solvents (in particular alcohols), under air atmosphere or under hydrogen bubbling. In particular, the reaction performed at 140° C. in air, using 1-hexanol or 2,4-dimethyl-3-pentanol (DMP) as solvents, led to allyl alcohol with yields of 28% and 61%, respectively using methyltrioxorhenium (MTO) as a catalyst, and to allyl alcohol with yields of 20% and 64%, respectively using $ReO_3$ as a catalyst. However, these catalysts exhibit a significant deactivation after only one run. Additionally, MTO is not easy to recover after use since it is dissolved in the liquid phase (homogeneous catalyst).

Some attempts have also been performed for using supported heterogeneous catalysts to carry out the transformation of glycerol to allyl alcohol. In particular, there are many reports about synthesis of allyl alcohol from glycerol using supported iron oxide-based solid catalysts in gas phase (see for instance Sánchez et al., Appl. Catal. B: Environmental 2014, 152-153, 117-128). However, according to these processes, the yields in allyl alcohol are limited to 32% (Wang et al., Chem. J. Chin. Univ. 2013, 34, 650-655).

OBJECTS AND SUMMARY

Hence, a reusable catalyst is still required to apply the reaction of deoxydehydration of glycerol into allyl alcohol at a practical scale and with a better yield.

A first subject-matter of the present invention is thus the use of an alumina-supported rhenium-oxide catalyst of formula $ReO_3/Al_2O_3$ (I), for catalysing the deoxydehydration of glycerol to allyl alcohol, said reaction being carried out in heterogeneous conditions in the presence of at least one aliphatic alcohol.

The catalysts of formula (I) above make it possible to carry out the deoxydehydration of glycerol into allyl alcohol at a practical scale with a yield up to about 90%, i.e. much higher than with the supported iron-oxide catalysts previously reported for the same reaction in the prior art. In addition, the catalysts of formula (I) are reusable and easily recoverable from the reaction medium.

Among the catalysts of formula (I) above, those in which the amount of $ReO_3$ ranges from about 5 to 15 weight % relative to the total mass of catalyst of formula (I) are preferred, more particularly, those in which the amount of $ReO_3$ ranges from about 8 to 12 weight %.

By way of example, the catalysts of formula (I) above can in particular be prepared by an incipient-wetness impregnation of alumina ($Al_2O_3$) with an aqueous solution of perrhenic acid ($HReO_4$). After impregnation, the resulting catalyst of formula (I) is preferably dried at a temperature ranging from about 100 to 150° C. for several hours and then calcinated.

Another subject-matter of the present invention is a process for the production of allyl alcohol from glycerol in the presence of a catalyst, said process comprising only one step of deoxydehydration of glycerol, said reaction being carried out in heterogeneous conditions, in the presence of i) an alumina-supported rhenium-oxide catalyst of formula $ReO_3/Al_2O_3$ (I) and of ii) at least one aliphatic alcohol.

The process in accordance with the invention makes it possible to produce allyl alcohol without the use of fossil resources-derived raw materials. It is simple to carry out (just one stage) and very selective. It results in allyl alcohol, with yields up to about 90%.

According to a preferred embodiment of the process of the invention, the catalyst of formula (I) is chosen among catalysts in which the amount of $ReO_3$ ranges from about 5 to 15 weight % relative to the total mass of catalyst of formula (I), and more particularly, among which those in which the amount of $ReO_3$ ranges from about 8 to 12 weight %.

According to a preferred embodiment of the invention, the specific surface area of the alumina used to support $ReO_3$ ranges from about 100 $m^2/g$ to 300 $m^2/g$ and more preferably still from 150 $m^2/g$ to 250 $m^2/g$ (B.E.T. method).

The aliphatic alcohol is used as a solvent. The aliphatic alcohol also plays the role of a sacrificial reducing agent during the conversion of glycerol into allyl alcohol.

According to a particular and preferred embodiment of the present invention, the aliphatic alcohol is a monohydroxylated alcohol having from 6 to 10 carbon atoms, preferably from 6 to 8 carbon atoms.

Among monohydroxylated alcohols having from 6 to 8 carbon atoms, secondary alcohols are preferred.

Among such secondary alcohols, one can mention 2-hexanol and 3-octanol.

According to a particular and preferred embodiment of the present invention, the aliphatic alcohol is 2-hexanol.

The deoxydehydration reaction is preferably carried out at a temperature higher than or equal to about 140° C. and more preferably at a temperature ranging from about 140 to 150° C. A temperature of about 145° C. is even more particularly preferred according to the invention.

According to a preferred embodiment of the process in accordance with the invention, the deoxydehydration reaction is carried out using glycerol with a purity of at least 95%. Indeed, the studies performed by the inventors have shown that the use of glycerol having a purity lower than 95%, i.e., containing more than 5 wt. % of impurities, in particular more than 5 wt. % of water, relative to the total weight of glycerol, unfavourably affects the yield in allyl alcohol.

After reaction, the separation of the co- and by-products of the reaction can be carried out by any appropriate technique known to a person skilled in the art, for example by distillation.

The recovery of the catalyst can be easily made, for example by filtration and then dried. Before a new use, and even if it is not compulsory, the catalyst can be calcinated.

DETAILED DESCRIPTION

The present invention is illustrated by the following examples, to which, however, it is not limited.

EXAMPLES

In the next examples, the following starting materials were used:
Glycerol, purity in water >99% (Aldrich)
Alumina ($\gamma$-$Al_2O_3$) having a surface area of 198.7 $m^2/g$ (B.E.T.) (Puralox),
Silicium dioxide ($SiO_2$) having a surface area of 105.5 $m^2/g$ (B.E.T.) (Fuji Silysia),
Titanium oxide ($TiO_2$) having a surface area of 62.5 $m^2/g$ (B.E.T.) commercialized under the name P25 (Aldrich, 99% purity),
75 w % perrhenic acid ($HReO_4$) aqueous solution (Aldrich),
1-hexanol (Aldrich),
2-hexanol (Aldrich),
1-octanol (Aldrich),
3-octanol (Aldrich,
2-butanol (Aldrich),
Cyclohexanol (Aldrich),
1-phenylethanol (Aldrich),
Benzyl alcohol (Aldrich).

All these materials were used as received from the suppliers, i.e., without any additional purification.

Preparation of Alumina-Supported Rhenium Oxide Catalysts of Formula (I) According to the Invention The different catalysts of formula (I) were prepared by an incipient-wetness impregnation method.

Catalysts of formula (I) containing respectively 5, 10 or 15 wt % of $ReO_3$ relative to the total amount of catalysts were prepared. These catalysts were respectively denoted 5 w %-$ReO_3$/$Al_2O_3$, 10 w %-$ReO_3$/$Al_2O_3$, and 15 w %-$ReO_3$/$Al_2O_3$.

For the preparation of 5 w %-$ReO_3$/$Al_2O_3$, 1.81 g of $\gamma$-$Al_2O_3$ were added to a diluted aqueous solution of $HReO_4$ resulting from the addition of 136 mg of the 75 w % perrhenic acid aqueous solution (Aldrich) in 1 mL of water.

For the preparation of 10 w %-$ReO_3$/$Al_2O_3$, 1.81 g of $\gamma$-$Al_2O_3$ were added to a diluted aqueous solution of $HReO_4$ resulting from the addition of 286 mg of the 75 w % perrhenic acid aqueous solution (Aldrich) in 1 mL of water.

For the preparation of 15 w %-$ReO_3$/$Al_2O_3$, 1.81 g of $\gamma$-$Al_2O_3$ were added to a diluted aqueous solution of $HReO_4$ resulting from the addition of 456 mg of the 75 w % perrhenic acid aqueous solution (Aldrich) in 1 mL of water.

After one hour, the impregnated catalysts were dried at 110° C. for 24 hours and calcinated under static air at 500° C. for 3 hours before their use in the catalytic tests.

Preparation of a $TiO_2$-Supported Rhenium Oxide Comparative Catalyst Not Forming Part of the Present Invention The same procedure as that described above for the preparation of catalysts of formula (I) has been used to prepare the comparative catalyst except that $TiO_2$ (1.81 g) was used instead of $Al_2O_3$.

After one hour, the as-obtained impregnated catalyst (denoted 5-w %-$ReO_3$/$TiO_2$) was dried at 110° C. for 24 hours and calcinated under static air at 500° C. for 3 hours before its use in the catalytic tests.

Example 1: Conversion of Glycerol to Allyl Alcohol Using 10-Wt % $ReO_3$/$Al_2O_3$ (First/Second and Third Uses of the Catalyst)

First Use:

A pressure-resistant glass tube equipped with a magnetic stirring bar was loaded with glycerol (92 mg, 1 mmol), 10-wt % $ReO_3$/$AL_2O_3$ (100 mg), and 2-hexanol (3.3 mL). The vessel was tightly sealed by a screw cap and the mixture was stirred (500 rpm) in an oil bath maintained at 170° C. for 2.5 h so that the reaction medium was maintained at a reaction temperature of 148° C. After reaction, the solution was cooled to room temperature and then diluted with 15 mL of methanol Biphenyl (20 mg, 0.13 mmol) was added to the solution as an internal standard for gas chromatography (GC) analysis. The solution was placed under ultrasonic irradiation for 10 min to assure a good homogeneity of the mixture. The conversion and yield were determined on the basis of the analysis of the mixture by GC.

The yield in allyl alcohol was 91%, the conversion of glycerol was >99%, and the selectivity to allyl alcohol (yield/conversion×100) was 91% (first use).

Second Use:

The reaction proceeded as above for the first use, using the spent 10-wt %-ReO$_3$/Al$_2$O$_3$ catalyst (82 mg) recovered from experiment 1 with a new amount of glycerol (75 mg) to keep the glycerol/catalyst ratio constant at the beginning of the reaction compared to the conditions of experiment 1 (first use).

The used 10-wt %-ReO$_3$/Al$_2$O$_3$ was re-calcined at 500° C. for 3 h before the second reaction. The yield in allyl alcohol was 93%, the conversion of glycerol was >99%, and the selectivity to allyl alcohol was 93%.

Another test was also performed using the spent 10-wt %-ReO$_3$/Al$_2$O$_3$ catalyst (82 mg) from experiment 1 (first use) with a new amount of glycerol (75 mg) but instead of carrying out calcination before the second use, only a drying at 110° C. was performed for 2 hours. The yield in allyl alcohol was 90%, the conversion of glycerol was >99%, and the selectivity to allyl alcohol was 90%. This additional result demonstrates that, even if a calcination step is preferably carried out before the reuse of the catalyst, such a calcination step is not compulsory at all to obtain good performances.

Third Use:

The reaction proceeded as described above for the second use, using the spent 10-wt %-ReO$_3$/Al$_2$O$_3$ catalyst (62 mg) recovered from experiment 2 (with calcination) with a new amount of glycerol (62 mg) to keep the glycerol/catalyst ratio as a constant at the beginning of the reaction compared to the conditions of experiment 1.

The used 10-wt %-ReO$_3$/Al$_2$O$_3$ was again re-calcined at 500° C. for 3 h before the third reaction.

The yield in allyl alcohol was 92%, the conversion of glycerol was >99%, and the selectivity to allyl alcohol was 92%.

These results demonstrate that the catalyst of formula (I) can be easily reused to give allyl alcohol with 93% or 92% yields, respectively, for the second and third uses. No peak assigned to acrolein or acrylic acid was observed in $^1$H NMR analysis of the products.

Example 2: Conversion of Glycerol to Allyl Alcohol Using 5-wt %-ReO$_3$/Al$_2$O, 10-wt %-ReO$_3$/Al$_2$O$_3$ and 15-wt %-ReO$_3$/Al$_2$O$_3$ The conversion of glycerol to allyl alcohol has been performed in the same conditions as those described in example 1 above (first use).

The results obtained with over of the catalysts of formula (I) are given in Table 1 below:

TABLE 1

| Catalyst (I) | Allyl alcohol Yield (%) | Glycerol Conversion (%) | Allyl alcohol Selectivity (%) |
| --- | --- | --- | --- |
| 5-wt%-ReO$_3$/Al$_2$O$_3$ | 77 | >99 | 77 |
| 10-wt%-ReO$_3$/Al$_2$O$_3$ | 91 | >99 | 91 |
| 15-wt%-ReO$_3$/Al$_2$O$_3$ | 88 | >99 | 88 |

Example 3: Conversion of Glycerol to Allyl Alcohol Using 5-wt %-ReO$_3$/Al$_2$O$_3$—Comparison with 5-wt %-ReO$_3$/TiO$_2$ In this example, the conversion performances of the 5-w %-ReO$_3$/Al$_2$O$_3$ of formula (I) according to the present invention were compared to that of a catalyst not being part of the present invention, namely 5-w %-ReO$_3$/TiO$_2$.

The conversion of glycerol to allyl alcohol was carried in the same conditions as those used in example 1, first use, unless otherwise stated.

The results are given in the following Table 2:

TABLE 2

| Catalyst | Allyl alcohol Yield (%) | Glycerol Conversion (%) | Allyl alcohol Selectivity (%) |
| --- | --- | --- | --- |
| 5-wt%-ReO$_3$/Al$_2$O$_3$ | 77 | >99 | 77 |
| 5-wt%-ReO$_3$/TiO$_2$ (*) | 82 | >99 | 82 |

(*) Comparative catalyst not forming part of the invention

As shown in Table 2, TiO$_2$ and Al$_2$O$_3$ supports showed high reactivity (82% and 77% yields to allyl alcohol for TiO$_2$ and Al$_2$O$_3$, respectively). While TiO$_2$ showed higher reactivity than Al$_2$O$_3$, it was not possible to reuse the ReO$_3$/TiO$_2$ catalyst because of rhenium leaching from the TiO$_2$ support.

Example 4: Conversion of Glycerol to Allyl Alcohol Using 10-wt %-Re$_3$/Al$_2$O$_3$ at Different Temperatures In this example, the conversion of glycerol to allyl alcohol was carried out using the same conditions as those in example 1 above, first use, but varying the temperature of the oil bath, so that the temperature of the reaction medium also varied.

The results are given in Table 3 below:

TABLE 3

| Example | Oil Bath temperature (° C.) | Reaction temperature (° C.) | Allyl alcohol Yield (%) | Glycerol Conversion (%) | Allyl alcohol Selectivity (%) |
| --- | --- | --- | --- | --- | --- |
| 4a | 150 | 140 | 75 | 89 | 84 |
| 4b | 170 | 148 | 91 | >99 | 91 |
| 4c | 180 | 148 | 90 | >99 | 90 |

Although 2-hexanol has, at atmospheric pressure, a boiling point (b.p.) of 139° C., the preferred reaction temperature is higher than 139° C.

The reaction with the same catalysts at a temperature of the oil bath of 150° C. (observed inner reaction temperature: 140° C.) gave allyl alcohol with a 75% yield. When the temperature of the oil bath was 170° C. (observed inner reaction temperature: 148° C.), allyl alcohol was obtained in excellent yield (91%).

Example 5: Conversion of Glycerol to Allyl Alcohol Using 10-wt %-ReO$_3$/Al$_2$O$_3$ in Aliphatic Alcohol Solvents—Comparison with Cyclic Alcohol Solvents In this example, the conversion of glycerol to allyl alcohol was carried out in the same conditions as those of example 1 (first use) but using different aliphatic alcohols according to the process of the invention, and in comparison with some cyclic alcohols according to a process not forming part of the present invention.

The results are tabulated in Table 4 below:

TABLE 4

| Alcohol | Allyl alcohol Yield (%) | Glycerol Conversion (%) | Allyl alcohol Selectivity (%) |
|---|---|---|---|
| 2-hexanol | 91 | >99 | 91 |
| 1-hexanol | 73 | >99 | 73 |
| 1-octanol | 45 | 93 | 48 |
| 3-octanol | 84 | 93 | 90 |
| 2-butanol | 40 | 51 | 78 |
| Cyclohexanol (*) | 30 | 52 | 58 |
| 1-phenylethanol (*) | 0 | 83 | 0 |
| Benzyl alcohol (*) | 8 | 85 | 9 |

(*) Comparative catalyst not forming part of the invention

These results show that all the aliphatic alcohols used as solvents according to the process of the present invention lead to allyl alcohol with a yield of at least 40%. However, among these alcohols, and for the same number of carbon atoms, secondary alcohols showed higher yields than primary alcohols. On the contrary, the use of cyclohexanol induced a yield lower than 40% and aryl alcohols (1-phenylethanol and benzyl alcohol) are not acceptable solvents of the deoxydehydration of glycerol to allyl alcohol in the presence of a catalyst of formula (I) since the yields were very low despite high conversions (0% and 8% yields when using 1-phenylethanol and benzyl alcohol, respectively).

Example 6: Conversion of Glycerol to Allyl Alcohol Using 10-wt %-ReO$_3$/Al$_2$O$_3$ Using Glycerol Exhibiting Different Fractions of Water In this example, the conversion of glycerol to allyl alcohol was carried out in 2-hexanol with 10-wt %-ReO$_3$/Al$_2$O$_3$ using glycerol containing different fractions of water, i.e., containing from less than 1 wt % to 20 wt % of water.

The glycerol solutions with different degrees of purity in water were simply prepared by adding the required amounts of water in purchased glycerol having a purity of >99%.

The corresponding results are tabulated in Table 5 below:

TABLE 5

| Purity of Glycerol in water (wt %) | Amount of added water (wt %) | Allyl alcohol Yield (%) | Glycerol Conversion (%) | Allyl alcohol Selectivity (%) |
|---|---|---|---|---|
| >99 | 0 | 91 | >99 | 91 |
| 95 | 5 | 91 | >99 | 91 |
| 85 | 16 | 80 | 93 | 86 |
| 80 | 23 | 66 | 93 | 71 |

These results show that the process of deoxydehydration of glycerol according to the present invention can be carried out with very good yield in allyl alcohol even if the glycerol exhibit a purity in water of only 80 wt %.

The invention claimed is:

1. A method for catalysing the deoxydehydration of glycerol to allyl alcohol, said method comprising:
   deoxydehydrating glycerol to allyl alcohol with an alumina-supported rhenium-oxide catalyst of formula ReO$_3$/Al$_2$O$_3$(I), wherein said reaction is carried out in heterogeneous conditions in the presence of at least one aliphatic alcohol.

2. The method of claim 1, wherein said at least one aliphatic alcohol is used as a solvent.

3. The method of claim 1, wherein said catalyst of formula (I) is chosen among those in which the amount of ReO$_3$ ranges from 5 to 15 weight % relative to the total mass of catalyst of formula (I).

4. A process for the production of allyl alcohol from glycerol in the presence of a catalyst, said process comprising only one step of deoxydehydration of glycerol, said reaction being carried out in heterogeneous conditions, in the presence of i) an alumina-supported rhenium-oxide catalyst of formula ReO$_3$/Al$_2$O$_3$(I) and of ii) at least one aliphatic alcohol.

5. The process of claim 4, wherein the catalyst of formula (I) is chosen among catalysts in which the amount of ReO$_3$ ranges from 5 to 15 weight % relative to the total amount of catalyst of formula (I).

6. The process of claim 4, wherein the aliphatic alcohol is a monohydroxylated alcohol having from 6 to 10 carbon atoms.

7. The process of claim 6, wherein the aliphatic alcohol is a monohydroxylated alcohol having from 6 to 8 carbon atoms.

8. The process of claim 7, wherein the monohydroxylated alcohol is a secondary alcohol.

9. The process according to claim 8, wherein the secondary alcohol is 2-hexanol or 3-octanol.

10. The process according to claim 3, wherein the deoxydehydration reaction is carried out at a temperature higher than or equal to 140° C.

11. The process according to claim 3, wherein the deoxydehydration reaction is carried out at a temperature ranging from 140 to 150° C.

* * * * *